(12) United States Patent
Nakanishi et al.

(10) Patent No.: US 6,971,680 B2
(45) Date of Patent: Dec. 6, 2005

(54) DIALYSIS COUPLER ASSEMBLY WITH JOINT MEMBERS AND HEMODIALYSIS SYSTEM USING SAME

(75) Inventors: Yoshihiko Nakanishi, Tokyo (JP); Kunihiko Yamanaka, Kitakyushu (JP); Hiromu Miura, Hiroshima (JP); Katsunori Masaoka, Hiroshima (JP); Takaaki Matsuo, Hiroshima (JP); Masahiro Taoka, Kitakyushu (JP); Sung-Teh Kim, Kitakyushu (JP)

(73) Assignees: Kitakyushu Institute of Biophysics Co., Ltd., Kitakyushu (JP); JMS Co., Ltd., Hiroshima (JP)

( * ) Notice: Subject to any disclaimer, the term of this patent is extended or adjusted under 35 U.S.C. 154(b) by 187 days.

(21) Appl. No.: 10/378,680

(22) Filed: Mar. 5, 2003

(65) Prior Publication Data

US 2004/0173515 A1 Sep. 9, 2004

(51) Int. Cl.[7] .............................................. F16L 25/00

(52) U.S. Cl. ........................... 285/9.2; 285/10; 285/18; 285/80; 285/95; 285/108; 285/110; 285/223; 285/325; 285/332; 210/232; 210/236

(58) Field of Search .............................. 285/9.2, 10, 18, 285/80, 95, 108, 110, 223, 325, 332; 210/232, 210/236

(56) References Cited

U.S. PATENT DOCUMENTS 5,810,718 A * 9/1998 Akiba et al. ................. 600/153

FOREIGN PATENT DOCUMENTS

| JP | 6-50485 | 2/1994 |
| JP | 9-51945 | 2/1997 |
| JP | 2001-314500 | 11/2001 |
| JP | 2002-345951 | 12/2002 |

* cited by examiner

Primary Examiner—W. L. Walker
Assistant Examiner—Krishnan S. Menon
(74) Attorney, Agent, or Firm—Westerman, Hattori, Daniels & Adrian, LLP

(57) ABSTRACT

The present invention provides a dialysis coupler assembly comprising a pair of rubber-like elastic tubular couplers, and a pair of joint members for joining the couplers together. Each of the couplers includes an inner channel 14 allowing a connector associated with a medical device to be fitted therein, and a smooth surface 15, 16 perpendicular to the longitudinal axis of the coupler. The couplers are adapted to be joined together through the joint members in such manner that the smooth surfaces are in liquid-tight contact with one another. Each of the joint members is adapted to be attached slidably and rotatably onto corresponding one of the couplers, the joint members having first and second engagement portions, respectively. The first and second engagement portions are disposed opposed to one another and adapted to cooperatively engage the joint members with one another so as to allow the smooth surfaces to be brought into liquid-tight contact with one another.

7 Claims, 2 Drawing Sheets

US 6,971,680 B2

DIALYSIS COUPLER ASSEMBLY WITH JOINT MEMBERS AND HEMODIALYSIS SYSTEM USING SAME

FIELD OF THE INVENTION

The present invention relates to a dialysis coupler assembly, and particularly to a coupler assembly for use in a pipeline of a hemodialysis system, comprising a pair of coupler, for example, one to be coupled to a nozzle associated with a blood purifier, and the other to be coupled to a hose. The present invention also relates to a hemodialysis system using such a dialysis couple assembly.

When used in a pipeline of a hemodialysis system, a coupler of the present invention can have a simplified inner structure, and achieve reliable connection with a nozzle attached to a blood purifier. When the coupler is detached from the nozzle and two of the coupler are cleaned while communicating there inner channels with each other, the couplers can be reliably cleaned even in the region where the nozzle was inserted, without any dead space in the inner channel having the risk of infection caused by bacteria without using a coupling rod.

BACKGROUND OF THE INVENTION

Generally, a hemodialyser for hemodialysis therapy uses a coupler for connecting a nozzle attached to a blood purifier and a piping for supplying/discharging dialysing liquid, to circulate the dialysing liquid and purify a blood.

In such a hemodialyser, it is particularly required to assure a reliable connection between the nozzle and the connector. For example, one conventional coupler, Hansen connector, includes a robber O-ring in the innermost recesses of its inner channel for receiving the nozzle therein. When a nozzle having a front end formed with an obliquely extending slit is inserted into the hollow portion, the front end tightly contacts the O-ring to prevent leakage of dialysing liquid.

The tight contact state between the O-ring and the nozzle is assured, for example, by the following dynamical mechanism. When a cylindrical slider attached on the outer periphery of the coupler is moved by a biasing force of a built-in spring, and superimposed on a plurality of ball bearings. The slider presses the ball bearings inward or toward the longitudinal axis of the coupler to apply the vertical force to the obliquely slit surface and to the inclined surface of the inserted front end of the nozzle. Thus, the applied force is changed in direction about 90 degrees to allow the inclined surface of the nozzle to be tightly pressed on the O-ring.

For cleaning, after detaching from the nozzle, two of the coupler are jointed together while communicating their inner channels with one another through a coupling rod with a nozzle [International Standard on dialysing-liquid ports (ISO 8637)] attached to the respective ends of the couplers.

While the above coupler has a structural advantage in that it can be detached from the nozzle only by moving the cylindrical slider along the outer periphery thereof, the structure of the inner channel is inevitably complicated due to additional components such as O-ring and ball bearings. In addition, the distal side of O-ring cannot contact cleaning liquid directly, and forms a hydrodynamical dead zone causing bacteria infection.

When the coupling rod is inserted into the couplers to join the couplers together during cleaning, the inserted portion covers some portions of the inner channels to interrupt the cleaning of such portions, resulting in undesirable infection. For example, bacteria or endotoxic is actually detected from the conventional coupler used to provide detachability in piping of dialysing liquid in hemodialysis for treating a patient of chronic renal failure, which raises concerns about harmful effect.

In order to solve the infection in the conventional coupler, there have been developed various couplers such as "Clean Coupler" (NIKKISO Co., Ltd.), "Antibacteria Coupler" (NIPRO), and "Silicon Coupler" (Toray Industries, Inc.). While these couplers have a certain level of anti-infection effect, a slight amount of endotoxic is detected after 1 to several weeks from setting, and their bacteriological cleanliness is not immaculate. These couplers are essentially required to use the coupling rod during cleaning. The detected infection would be caused by non-cleaned portion contacting the coupling rod.

SUMMARY OF THE INVENTION

It is therefore an object of the present invention to provide a dialysis coupler, and particularly to a coupler for use in a pipeline of a hemodialysis system, capable of achieving a liquid-tight coupling with a simplified inner structure without any complicated component, such as O-ring or ball bearings, and of eliminating the need for using coupling rod during cleaning, and reducing the risk of infection caused by interfusion or proliferate of bacteria or endotoxic In order to achieve this object, the present invention provides a dialysis coupler assembly comprising a pair of rubber-like elastic tubular couplers, and a pair of joint members for joining the couplers together. Each of the couplers includes an inner channel allowing a connector associated with a medical device to be fitted therein, and a smooth surface perpendicular to the longitudinal axis of the coupler. The couplers are adapted to be joined together through the joint members in such manner that the smooth surfaces are in liquid-tight contact with one another. Each of the joint members is adapted to be attached slidably and rotatably onto corresponding one of the couplers, the joint members having first and second engagement portions, respectively. The first and second engagement portions are disposed opposed to one another and adapted to cooperatively engage the joint members with one another so as to allow the smooth surfaces to be brought into liquid-tight contact with one another.

In the above structure, the couplers may be adapted to be joined together through the joint members in such manner that the smooth surfaces are in compressively liquid-tight contact with one another.

Further, the first engagement portion may be formed as at least two of convex portions protruding from corresponding the joint member along the longitudinal axis of the coupler. Each of the convex portions may include a pawl extending in the circumferential direction of the coupler. The second engagement portion may be formed as at least two of concave portions for receiving therein the convex portions, respectively, each of the concave portions including a recess to be engaged with the pawl. In this case, wherein when the smooth surfaces are in compressively liquid-tight contact with one another, the convex portions are fitted with corresponding the concave portions while engaging the pawls with corresponding the recesses.

Each of the pawl and recess may have an engagement surface tapered in the circumferential direction.

The convex portions and corresponding the concave portions may be disposed on the outer periphery of the couplers to allow the convex portions and the corresponding concave portions to be moved slidably and rotatably the outer periphery of the couplers in such manner that the convex portions are fitted in or released from corresponding concave portions, and the pawls are engaged with or disengaged from corresponding the recesses.

The joint members may be adapted to fix or hold the smooth surfaces in their liquid-tight contact state.

The joint members may be adapted to fix or hold the smooth surfaces in their liquid-tight contact state at a predetermined position.

Each of the couplers may include a stopper portion for preventing the joint members from dropping therefrom.

The present invention also provides a hemodialysis system using the dialysis coupler as described above.

Coupling Between Couplers

If the present invention, the dialysis coupler is made of material having a rubber-like elasticity. By taking advantage of this property, when the couplers are coupled or jointed with one another, the smooth surfaces formed on their joint surface perpendicularly to the longitudinal axis of the couplers are first disposed opposed to one another. Then, the joint members are slidably moved toward the smooth surfaces to compressively press it from behind and engaged the engagement portions of the joint members with one another while maintaining the tight contact between the smooth surfaces, so that the couplers can be liquid-tightly jointed together. This structure allows the couplers to be liquid-tightly jointed together without using O-ring or ball bearings. Thus, the couplers can be liquid-tightly jointed together with a simplified inner structure.

As above, in the dialysis coupler assembly of the present invention, no component such as O-ring or ball bearings is attached on the inner surface of the coupler. Thus, the inner surface of the coupler is simplified, and the risk of infection caused by bacteria on the distal side from O-ring can be avoided.

The dialysis coupler assembly of the present invention can form a circulation circuit without using any bypass plug such as a coupling rod to reduce the risk of infection caused by insertion of the bypass plug.

Engagement Between Couplers and Joint Member

While the dialysis coupler assembly of the present invention has a tight contact region between a connector of medical devices and the surface of the inner channel, the tight contact state can be assured by means of the rubber-like elastic material of the coupler itself without using O-ring or ball bearings. Thus, the tight contact between the connector of medical devices and the couplers can be achieved without dead zone causing proliferates of bacteria.

The dialysis coupler assembly of the present invention has no troublesome component such as O-ring or ball bearings, and the coupler itself has rubber-like elasticity. Thus, the steps in the inner structure of the inner channel can be more smoothened.

DESCRIPTION OF THE PREFERRED EMBODIMENT

Figure 1:
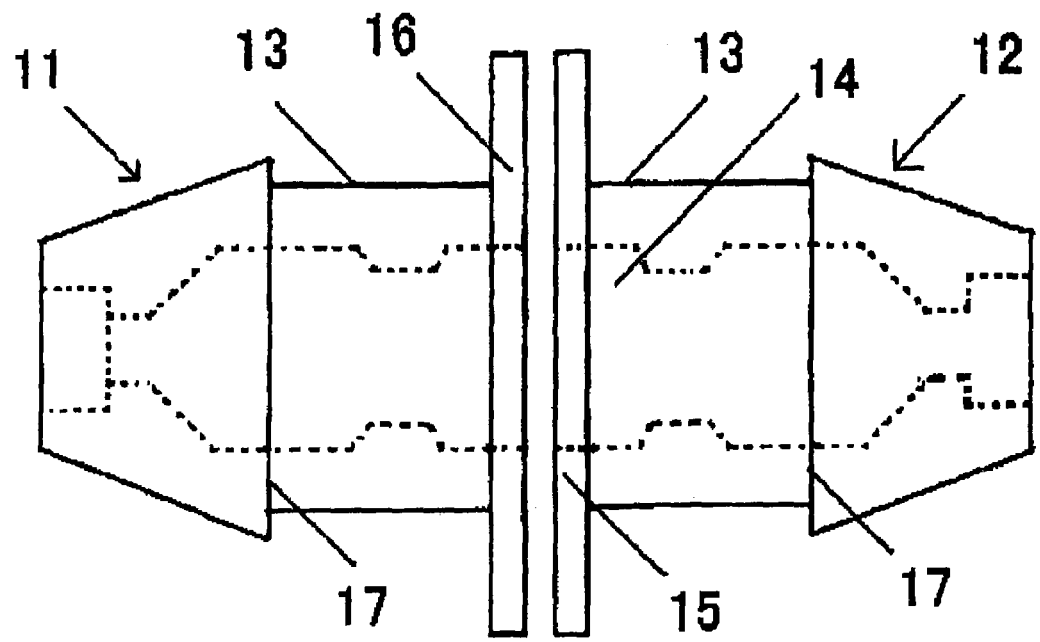
FIG. 1 is a front view of couplers of a coupler assembly according to one embodiment of the present invention.
Figure 2:
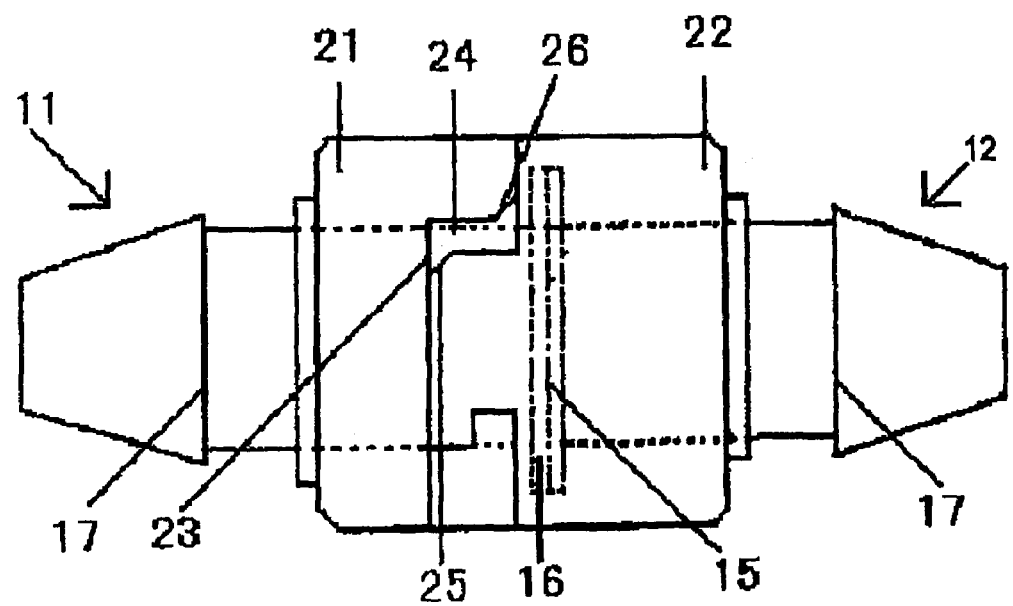
FIG. 2 is a front view a coupler assembly according to one embodiment of the present invention, wherein the couplers in FIG. 1 are jointed together through joint members.
Figure 3:
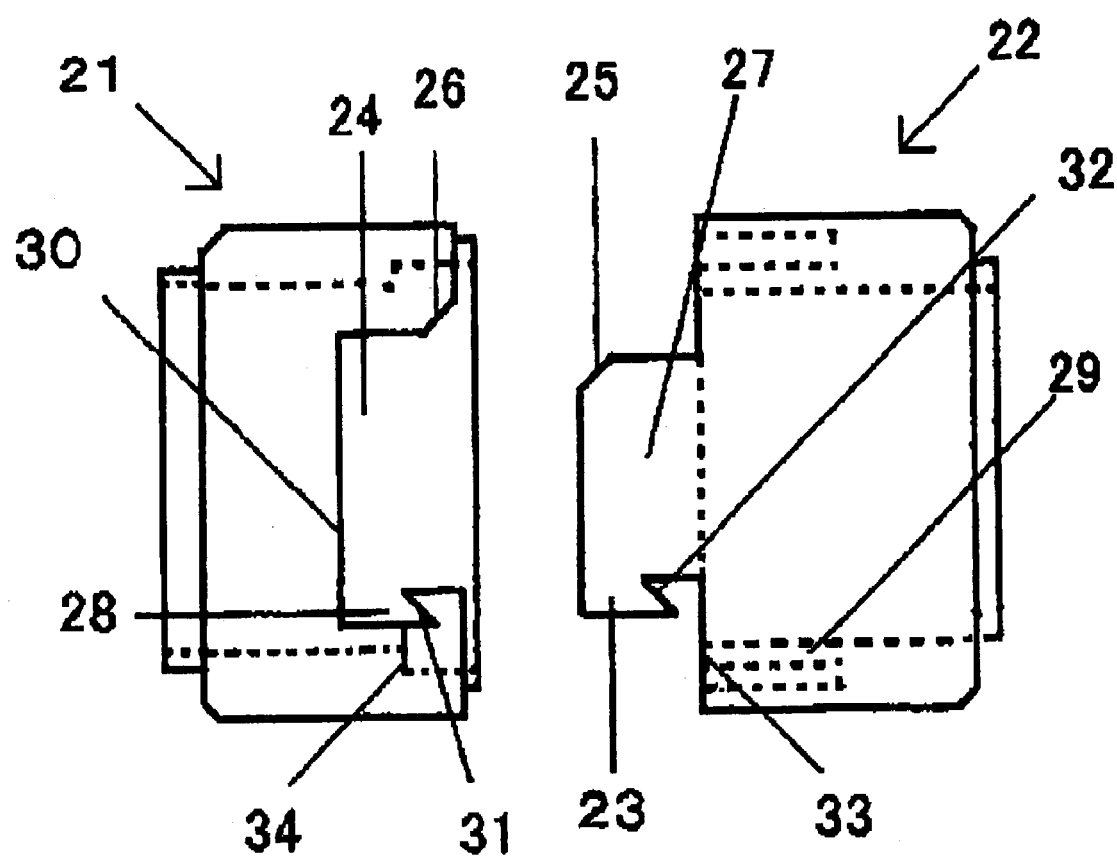
FIG. 3 is a front view of the joint members in FIG. 2.

With reference to FIGS. 1 to 3, a dialysis coupler assembly having joint members according to one embodiment of the present invention will be described.

FIG. 1 is a front view of dialysis couplers according to one embodiment of the present invention. The reference numerals 11, 12 indicate a pair of robber-like elastic couplers. The material of the coupler includes silicon gum or any other elastomer, preferably silicon gum having neither physical nor chemical action with dialysing liquid.

In FIG. 1, the reference numeral 13 indicates a region where a pair of joint members are attached slidably and rotatably. The reference numeral 14 indicates inner channel for allowing a nozzle attached to a blood purifier to be fitted therein. The reference numerals 15, 16 indicate a pair of smooth surfaces perpendicular to the longitudinal axis of the coupler. The smooth surfaces 15, 16 are brought into tight contact with one another through the joint members. The elasticity, smoothness and area of the vertical smooth surfaces 15, 16 may have be arranged to achieve adequate liquid-tightness therebetween when the joint members are slidably moved toward the smooth surfaces.

While each of the rubber-like elastic couplers 11, 12 including the vertical smooth surfaces 15, 16 is preferably formed integrally, only the smooth surface 15, 16 may be made of a suitable material for achieve the liquid-tight contact.

The reference numeral 17 in FIG. 1 indicates a stopper portion for preventing the drop-off of joint members inserted in the region 13 slidably and rotatably.

Joint Member

FIG. 2 is a front view showing the state when first and second joint members 21, 22 are fitted on the region 13 of the coupler 13 in FIG slidably and rotatably. FIG. 3 is a view showing the disengaged interlock devices 21, 22.

In FIGS. 2 and 3, in the first joint member 21, a concave portion 30 is formed on the outer surface 24 of the tubular coupler to allow a convex portion 27 of the second joint member 22 to be fitted therein. A tapered portion 26 is provided at the inlet of the concave portion 30 for allowing the convex portion 27 of the second joint member 22 to pass through. Corresponding to the tapered portion 26, a taper portion 25 is also provided at the top edge of the convex portion 27 of the joint member 22. The tapered portions 25, 26 allow the convex portion 27 of the second joint member 22 to be smoothly fitted in the concave portion 30 of the first joint member 21.

The inner channel of the first joint member 21 has a wall 34 for fixing/holding the vertical smooth surfaces 15, 16 and the front wall 33 of a cylindrical section 29 of the second joint member 22 in the tight contact.

The respective position of the wall 33 and the wall 34 can be changed in the longitudinal axis to define the position at which the smooth surfaces 15, 16 is held and maintained in the tight contact.

The second joint member is a tubular member having the convex portion 27 to be fitted in the concave portion 30 of the first joint 21, as described above. The cylindrical section 29 formed includes inside the second joint member 22 has the front wall 33 for positioning and holding the smooth surfaces of the couplers in cooperation with the wall 34. That is, the smooth surfaces of the couplers are fixed and held by the wall 34 and the front wall 33 of the cylindrical section 29 in the tight contact state.

A recess 28 is formed in the concave portion 30 of the first joint member 21, and a pawl 23 is formed in the convex portion 27 of the second joint member 22. After fitting the convex portion 27 into the concave portion 30 the first and/or second joint members can be rotated to engage the pawl 23 with the recess 28.

The engagement between the pawl 23 and the recess 28 is strengthened by the elastic repulsive force of the couplers pressed/compressed by the joint members 21,22 to provide more reliable engagement between the joint members 21,22.

As shown in FIG. 3, the respective contact portions of the pawl 23 and the recess 28 are formed as tapered sections 31, 32 to effectively prevent the joint members from rotating causing disengagement between the joint members.

As described above, the concave portion 30 is integrally formed on the outer surface 25 of the tubular coupler. The fitting between the concave portion 30 of the joint member 21 and the convex portion 27 of the joint member 22, and the engagement between pawl 23 and the recess 28 of the can be achieved by moving them on the outer surface of the tabular coupler slidably or rotatably. Thus, the fitting and engagement operations can be performed smoothly, and the fitting and engagement states can be stably maintained.

Differently from the coupler, harder plastic is used as material of the joint members 21, 22.

As mentioned above, the couplers are jointed together in the liquid-tight state. Thus, couplers of the present invention can have a simplified inner structure without O-ring or ball bearings. Further, the cleaning operation can be performed without coupling rod to reduce the risk of infection caused by interfusion or proliferate of bacteria endotoxic. Furthermore, the present invention can provide a dialysis coupler capable of being readily and reliably coupled in the liquid-tight state, and a dialysis coupler assembly with joint member having means for joining together a series of couplers, particularly couplers used in a pipeline of a hemodialysis system, readily and reliably.

What is claimed is:

1. A dialysis coupler assembly comprising a pair of rubber-like elastic tubular couplers, and a pair of joint members for joining said couplers together, wherein each of said couplers includes an inner channel allowing a connector associated with a medical device to be fitted therein, and a smooth surface perpendicular to the longitudinal axis of said coupler, said couplers being adapted to be joined together through said joint members in such manner that said smooth surfaces are in liquid-tight contact with one another, and each of said joint members is adapted to be attached slidably and rotatably onto corresponding one of said couplers, said joint members having first and second engagement portions, respectively, wherein said first and second engagement portions are disposed opposed to one another and adapted to cooperatively engage said joint members with one another so as to allow said smooth surfaces to be brought into liquid-tight contact with one another, said first engagement portion is formed as at least two of convex portions protruding from corresponding said joint member along the longitudinal axis of said coupler, each of said convex portions including a pawl extending in the circumferential direction of said coupler;

said second engagement portion is formed as at least two of concave portions for receiving therein said convex portions, respectively, each of said concave portions including a recess to be engaged with said pawl, wherein when said smooth surfaces are in compressively liquid-tight contact with one another, said convex portions are fitted with corresponding said concave portions while engaging said pawls with corresponding said recesses, wherein each of said pawl and recess has an engagement surface tapered in the circumferential direction.

2. A dialysis coupler assembly as defined in claim 1, wherein said couplers are adapted to be joined together through said joint members in such manner that said smooth surfaces are in compressively liquid-tight contact with one another.

3. A dialysis coupler assembly as defined in claim 2, wherein said convex portions and corresponding said concave portions are disposed on the outer periphery of said couplers to allow said convex portions and said corresponding concave portions to be moved slidably and rotatably the outer periphery of said couplers in such manner that said convex portions are fitted in or released from corresponding concave portions, and said pawls are engaged with or disengaged from corresponding said recesses.

4. A dialysis coupler assembly as defined in either one of claim 1 or 2, wherein said joint members are adapted to fix or hold said smooth surfaces in their liquid-tight contact state.

5. A dialysis coupler assembly as defined in claim 4, wherein said joint members are adapted to fix or hold said smooth surfaces in their liquid-tight contact state at a predetermined position.

6. A dialysis coupler assembly as defined in either one of claim 1 or 2, wherein each of said couplers includes a stopper portion for preventing said joint members from dropping therefrom.

7. A hemodialysis system using the dialysis coupler as defined in either one of claim 1 or 2.

* * * * *